United States Patent
Yoshida (10) Patent No.: US 7,449,017 B2
(45) Date of Patent: Nov. 11, 2008

(54) DISPOSABLE DIAPER HAVING FASTENING SHEETS WITH PERFORATED TEAR LINES

(75) Inventor: Hideaki Yoshida, Tochigi (JP)

(73) Assignee: Daio Paper Corporation, Shikokuchuo-shi (JP)

( * ) Notice: Subject to any disclaimer, the term of this patent is extended or adjusted under 35 U.S.C. 154(b) by 0 days.

(21) Appl. No.: 10/580,694

(22) PCT Filed: Nov. 26, 2004

(86) PCT No.: PCT/JP2004/017570

§ 371 (c)(1), (2), (4) Date: May 25, 2006

(87) PCT Pub. No.: WO2005/051276

PCT Pub. Date: Jun. 9, 2005

(65) Prior Publication Data

US 2007/0129700 A1 Jun. 7, 2007

(30) Foreign Application Priority Data

Nov. 28, 2003 (JP) ............................. 2003-399515

(51) Int. Cl.
*A61M 35/00* (2006.01)
(52) U.S. Cl. .................. 604/389; 604/390; 604/386; 604/385.01
(58) Field of Classification Search ................ 428/132; 604/385.11, 385.01, 380, 382, 385.03, 385.04, 604/386–392
See application file for complete search history.

(56) References Cited

U.S. PATENT DOCUMENTS

| | | | | |
|---|---|---|---|---|
| 2,134,977 A | * | 11/1938 | Lankenau | .................. 604/401 |
| 2,862,251 A | * | 12/1958 | Kalwaites | .................. 264/119 |
| 4,063,559 A | * | 12/1977 | Tritsch | ........................ 604/390 |
| 4,850,988 A | * | 7/1989 | Aledo et al. | ........... 604/385.21 |
| 5,370,634 A | * | 12/1994 | Ando et al. | ............ 604/385.21 |
| 6,575,949 B1 | * | 6/2003 | Waksmundzki et al. | ...................... 604/385.11 |
| 2002/0032427 A1 | * | 3/2002 | Schmitz et al. | ........ 604/385.11 |
| 2002/0048652 A1 | * | 4/2002 | Malchow et al. | ............ 428/194 |
| 2002/0165514 A1 | * | 11/2002 | Datta et al. | ............ 604/385.11 |

FOREIGN PATENT DOCUMENTS

| | | |
|---|---|---|
| JP | 63-249704 | 10/1988 |
| JP | 6-31725 | 4/1994 |
| JP | 6-31726 | 4/1994 |
| JP | 2002-045214 | 2/2002 |
| JP | 2002-095693 | 4/2002 |
| JP | 2004-057541 | 2/2004 |

\* cited by examiner

*Primary Examiner*—Michele Kidwell
(74) *Attorney, Agent, or Firm*—Jordan and Hamburg LLP (57) ABSTRACT

A disposable diaper, which has fastening sheets on two side portions of a back side and which can be used with an ordinary fastening method but also a cross fastening method. The diaper has fastening sheets individually formed on the two side portions of the back side of the diaper and each including: joint ears formed to extend from outer side edges of each one of the sheets and to protrude sideward at two upper and lower stages; and facing fasteners disposed on inner sides of said joint ears, whereby the disposable paper diaper is worn on a body by fixing joint ears on a surface of an abdomen side of the diaper. Perforations leading from an outer side edge to an inner side are formed in a portion of the fastening base sheet between the joint ears. In perforations, a first perforation section extends from the outer side edge to an intermediate point P is a high tearing strength section $S_0$ having a relatively coarse perforation interval, and a second perforation section from intermediate point P to an inner end is a low tearing strength section $S_1$ having a relatively fine perforation interval.

8 Claims, 8 Drawing Sheets

FIG 11

DISPOSABLE DIAPER HAVING FASTENING SHEETS WITH PERFORATED TEAR LINES

BACKGROUND

The present invention relates to a disposable paper diaper comprising panel-shaped fastening sheets individually formed on the two side portions of the back side of the paper diaper and each including: joint ears formed to extend from the outer side edges of one sheet and to protruded sideward at two upper and lower stages; and adhesive layers or facing fasteners disposed on the inner sides of the joint ears and, more particularly, to a disposable paper diaper, in which the panel fastening sheets improper in the prior art for a cross fastening can also match the cross fastening.

Figure 8:
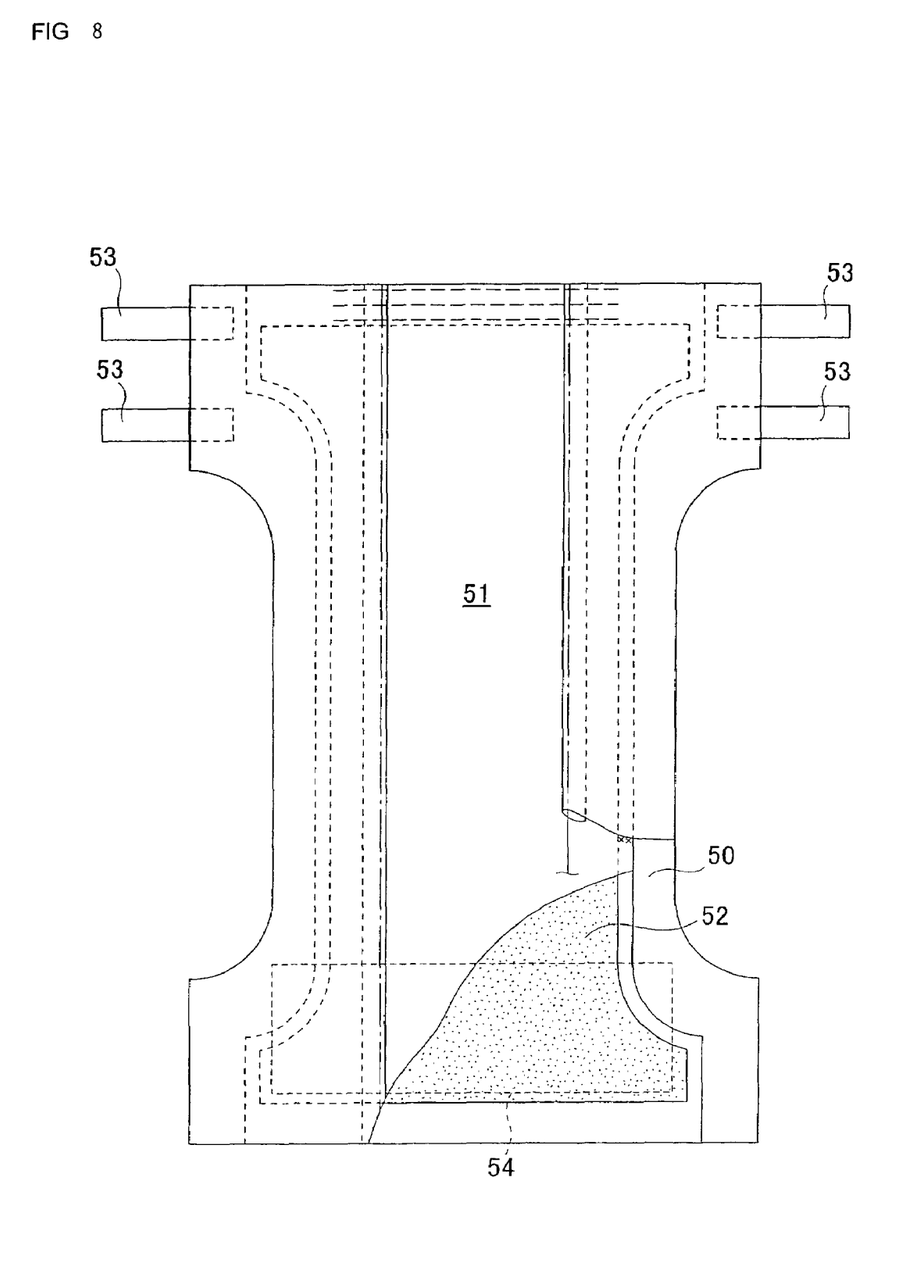
FIG. 8 shows a partially broken development of a tape type paper diaper of the prior art.

Mainly in an adult's tape type paper diaper commercially available in the art, as shown in FIG. 8, a pair of upper and lower fastening tapes 53 and 53 are so individually attached to the two side portions of the back side of the paper diaper, in which an absorbent 52 is sandwiched between an liquid-impermeable back sheet 50 and a liquid-permeable surface sheet 51, as to protrude sideway. The paper diaper is worn on a body by fastening those paired fastening tapes 53 and 53 to a front target sheet 54 on the surface of an abdomen side (as referred to the following Patent Documents 1 and 2, for example). Here, an adhesive or a facing fastener is employed as the means for adhering the fastening tapes 53 and 53.

Figure 9:
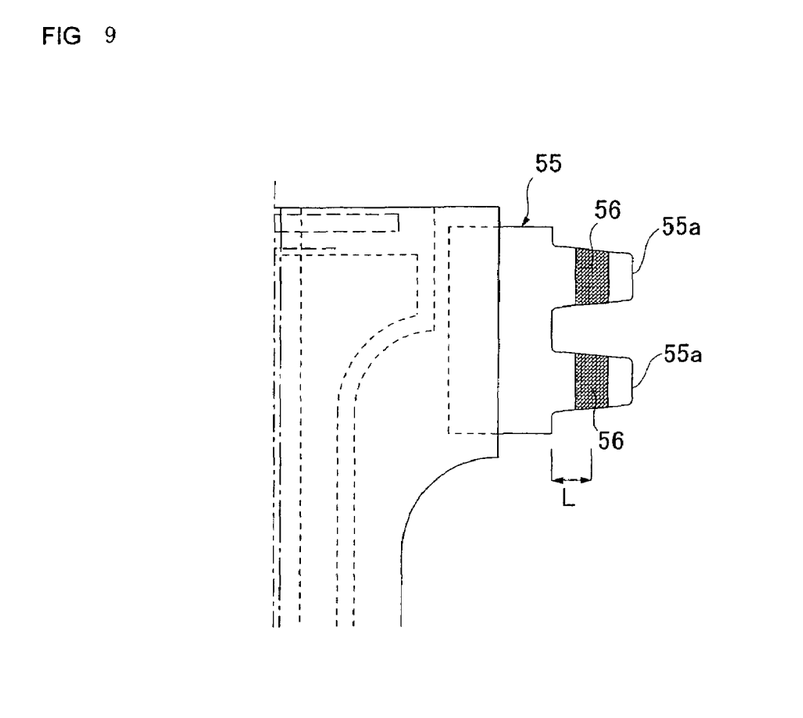
FIG. 9 shows a development showing an example of a panel-shaped fastening sheet 55 of the prior art.
Figure 10:
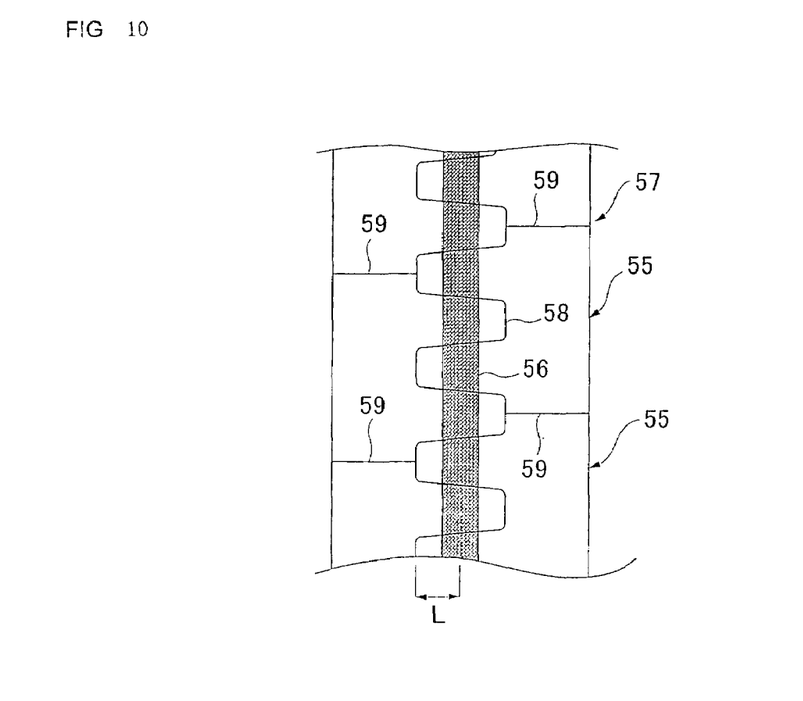
FIG. 10 shows a diagram showing a procedure for manufacturing the panel-shaped fastening sheet 55 by a zero-trim method.

In order to improve the appearance design and to solve the problem that the skin might otherwise be damaged by the leading end tips, moreover, the aforementioned band-shaped fastening tapes 53 are replaced in recent years by fastening sheets 55 (as referred to the following Patent Document 3), in which joint ears 55a and 55a are formed to extend from the outer side edges of one sheet and to protrude sideway at two upper and lower stages and in which an adhesive layer 56 is formed on the inner face sides of the joint ears 55a and 55a, as shown in FIG. 9. In the same Document, moreover, there is also disclosed a method for manufacturing the fastening sheets 55, as shown in FIG. 10. In this method, a continuous sheet 57 of a predetermined width is let off, and the adhesive layer 56 is continuously formed on the central portion of the continuous sheet 57. After this, the continuous sheet 57 is cut along an undulating periodic curve 58, which is so continuous in the longitudinal direction of the continuous sheet 57 as to cross the adhesive layer 56 alternately. At the same time, the continuous sheet 57 is cut at such predetermined positions along horizontal cutting lines 59 leading from the outer side edge to the undulating periodic curve 58 as to form the desired fastening sheet shape, thereby to form the individual fastening sheets 55, 55, - - - , and so on. According to this manufacturing method, the fastening sheets 55 can be efficiently manufactured without any waste on the sheet material. Here, this manufacturing method is called the "zero-trim method" because it forms no trim (i.e., a waste portion to be disposed).

When the adult's tape type paper diaper shown in FIG. 8 is to be worn, the wearer either adheres, in accordance with the body shape, the two upper and lower fastening tapes 53 and 53 generally in parallel to the target sheet 54 (by the ordinary fastening method) or adheres the two upper and lower fastening tapes 53 and 53 in a crossing manner to the target sheet 54 (as will be called the cross fastening method). The former fastening method is most employed by persons of a standard or fat body shape, but the latter fastening method is most employed by persons of a slim body shape.

Patent Document 1: JP-UM-A-6-31726,

Patent Document 2: JP-A-2002-95693, and

Patent Document 2: JP-A-63-249704.

SUMMARY OF THE INVENTION

As shown in FIG. 9, a fastening sheet 55 having joint ears of two upper and lower stages extending from the outer side edge of the single sheet is used because the zero-trim method can be applied thereto while wasting no material, but is not suited for the cross fastening method.

Figure 11:
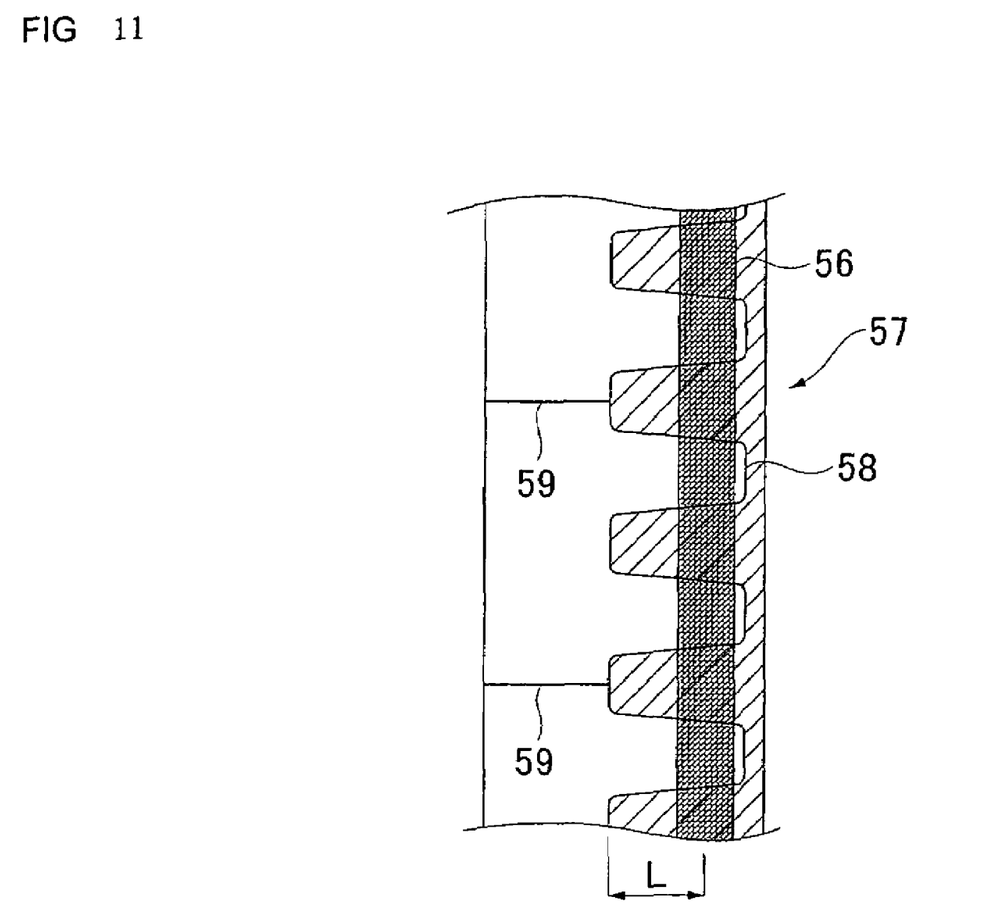
FIG. 11 shows a diagram showing a procedure for manufacturing the fastening sheet 55, as suited for the cross fastening method.

In order to match this cross fastening method, more specifically, it is necessary to reserve a protruding length for the joint ears 55a thereby to retain a distance L from the root ends of the joint ears 55a to the adhesive layer or the facing fastener. In the case of the zero-trim method, however, there is a problem that the position for forming the adhesive layer or the facial fastener is restricted to the central position of the continuous sheet 57 so that it cannot be arranged on the leading end sides of the joint ears 55a. In order that the fastening sheet 55 having the two upper and lower joint ears at the outer side portions of one sheet may match the cross fastening method, therefore, a suitable method is enable to arrange the adhesive layer or the facing fastener 56 at the leading end of the joint ear 55a, as shown in FIG. 11, by offsetting the adhesive layer or the facial fastener tape 56 on one side and by offsetting the undulating periodic curve 58 on one side. In this case, however, the hatched portions to become the trim are disposed to waste the sheet material.

Therefore, a main object of the invention is to enable a disposable paper diaper, in which fastening sheets having joint ears of two upper and lower stages extending from the outer side edges of one sheet are arranged on the two side portions of a back side, to cope at will with not only the ordinary fastening method but also the cross fastening method.

In order to solve the aforementioned problem, according to the invention, there is provided a disposable paper diaper comprising fastening sheets individually formed on the two side portions of the back side of the paper diaper and each including: joint ears formed to extend from the outer side edges of one sheet and to protrude sideward at two upper and lower stages; and adhesive layers or facing fasteners disposed on the inner sides of the joint ears, whereby the disposable paper diaper is worn on a body by fixing the joint ears on the surface of the abdomen side of the paper diaper, wherein perforations leading from the outer side edge to the inner side are formed in the portion of a fastening base sheet between the joint ears.

In the disposable paper diaper as set forth above, according to a feature of the invention, a first perforation section from the outer side edge to an intermediate point is a high tearing strength section having a relatively coarse perforation interval, and a second perforation section from the intermediate point to the inner end is a low tearing strength section having a relatively fine perforation interval.

In the disposable paper diaper as set forth above, according to a feature of the invention, the first perforation section has a tearing strength of 3 to 10 N, and wherein the second perforation section has a tearing strength of 0.01 to 6 N.

In the disposable paper diaper as set forth above, according to a further feature of the invention, the perforations are so worked at their inner end portions as to prevent the inner end from being torn out from the inner end.

In the disposable paper diaper as set forth above, according to a further feature of the invention, notches formed between the joint ears of the two upper and lower stages have a symmetric shape with respect to the shape of the joint ears.

In the invention as set forth above, the perforations leading from the outer side edge to the inner side are formed in the portion of a fastening base sheet between the joint ears. If the perforations are torn, therefore, the substantial distance L from the root ends of the joint ears to the adhesive layer or the facing fastener can be sufficiently retained to match the cross fastening method.

In the invention as set forth above, the first perforation section from the outer side edge to an intermediate point is a high tearing strength section having a relatively coarse perforation interval, and the second perforation section from the intermediate point to the inner end is a low tearing strength section having a relatively fine perforation interval. As a result, the perforations are not torn so long as they are not forcibly torn with an intention. If the perforations are intentionally torn from the outer side edge to the intermediate point, they can be easily torn out because the remaining perforation section is weakened in the tearing strength.

In the invention as set forth above, the first perforation section has a tearing strength of 3 to 10 N, and wherein the second perforation section has a tearing strength of 0.01 to 6 N. The first perforation section preferably has a tearing strength of 4 to 8 N, and the second perforation section preferably has a tearing strength of 0.01 to 2 N. The desired effects can be attained by setting the tearing strengths of the individual perforation sections within the aforementioned numerical ranges.

In the invention as set forth above, the perforations are so worked at their inner end portion as to prevent the inner end from being torn out from the inner end. As a result, it is possible to prevent the fastening sheet from being torn over the inner end of the perforations.

In the invention as set forth above, the notches formed between the joint ears of the two upper and lower stages have a symmetric shape with respect to the shape of the joint ears. Therefore, the present fastening sheet can be manufactured by the zero-trim method.

DETAILED DESCRIPTION

Figure 1:
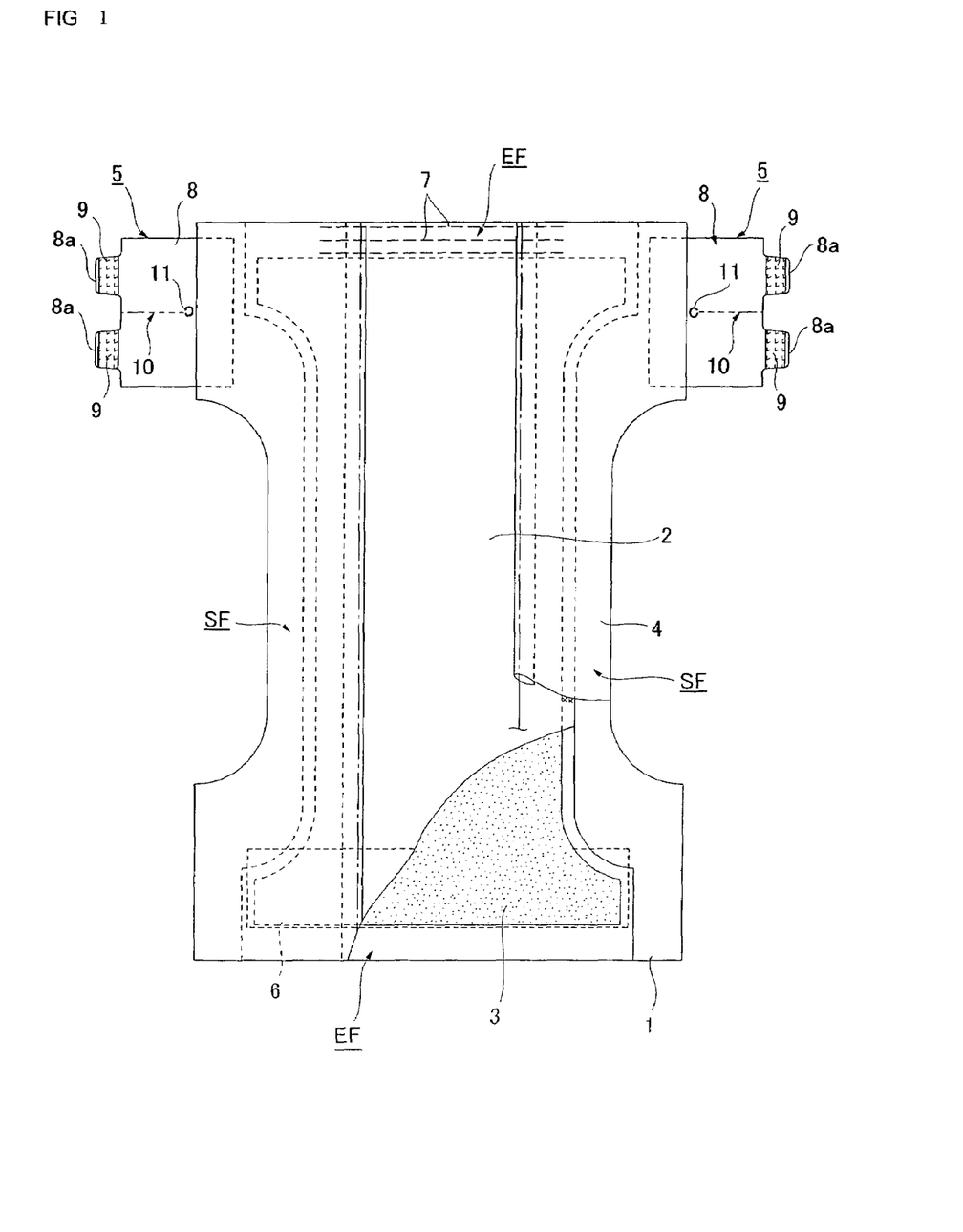
FIG. 1 shows a partially broken development of a paper diaper according to the invention.

Modes of embodiment of the present invention will be described in detail with reference to the accompanying drawings. FIG. 1 is a partially broken development of a paper diaper according to the invention.

In FIG. 1, the paper diaper is constituted to include a liquid-impermeable back sheet 1 made of polyethylene or the like, a liquid-permeable top sheet 2 made of a nonwoven fabric, and an absorbent 3 made between the back sheet 1 and the liquid-permeable top sheet 2 and made of flocculent pulp or the like and formed into a rectangular shape or a sandglass shape, for example, to have a rigidity. The absorbent 3 can be so wrapped with (not-shown) crape paper as to keep its shape. The liquid-impermeable back sheet 1 used in recent years has a moisture permeability so as to prevent stuffiness. This water/moisture-impermeable sheet is a finely porous sheet, which is prepared by melting and blending an inorganic filler into an olefin resin such as polyethylene or polypropylene to form a sheet and by orienting the sheet monoaxially or biaxially.

On the other hand, the liquid-permeable top sheet 2 used is exemplified by a porous or unporous nonwoven fabric or a porous plastic sheet. The material fibers forming the nonwoven fabric can be synthetic fibers of an olefin, polyester or amide group such as polyethylene or polypropylene, reproduced fibers such as rayon or cupro-ammonium rayon, or natural fibers such as cotton.

The liquid-impermeable back sheet 1 is extended outward from the periphery of the absorbent 3 to form a sandglass shape generally, and its side extensions form, together with the side portions of a barrier sheet 4, side flap portions SF having no absorbent. The liquid-permeable top sheet 2 is formed into a sandglass shape slightly larger than the absorbent 3, and its portions extending slightly outward from the side edges of the absorbent 3 are sandwiched between the barrier sheet 4 and the liquid-impermeable back sheet 1 and fixed on the side of the liquid-impermeable back sheet 1 by means of a hot-melt adhesive. The material used to form the barrier sheet 4 can be a plastic sheet or a melt-blown nonwoven fabric. In respect of a skin feeling, however, a material to be suitably used is prepared by making the nonwoven fabric water-repellent with silicone.

At the two longitudinal end portions, i.e., on the abdomen side and the back side of the paper diaper, on the other hand, both the liquid-impermeable back sheet 1 and the liquid-permeable top sheet 2 are extended to form end flap portions EF, in which the absorbent 3 is absent. Of these, the backside end flap portion EF has a plurality of, i.e., three filamentous, elastically extensible members 7, 7, - - - , and so on arranged along the widthwise direction. These filamentous, elastically extensible members 7 to be used can be made of materials such as styrene group rubber, olefin group rubber, urethane group rubber, ester group rubber, polyurethane, polyethylene, polystyrene, styrene-butadiene, silicone or polyester.

On the other hand, fastening sheets 5 and 5 are individually attached to the two end portions of the end flap portions EF on the backside, and a front target tape 6 is adhered along the widthwise direction to the surface of the abdomen side of the paper diaper. Thus, the paper diaper is worn on the body by fastening joint ears 8a of the fastening sheets 5 to that front target tape 6.

The fastening sheet 5 is attached by adhering the inner end side of one fastening base sheet 8 to the paper diaper side, and is provided at its leading end side with the joint ears 8*a* and 8*a* extending at two upper and lower stages from the outer side edges. The fastening sheet 5 to be used can be made of various sheet materials, and is preferably made of a nonwoven fabric of one or more layers having a basic weight of 40 to 80 g/m$^2$. The working method preferred is the span bond which is excellent in strength characteristics.

Male side facing fasteners 9 and 9 are individually attached to the inner face sides of the joint ears 8*a* and 8*a* (on the side of the liquid-permeable surface sheet 2) so that they can be jointed to the front target tape 6 constituting the female side facing fastener. Alternatively, the male side facing fasteners 9 may be located on the female side whereas the front target tape 6 may be located on the male side.

Figure 4:
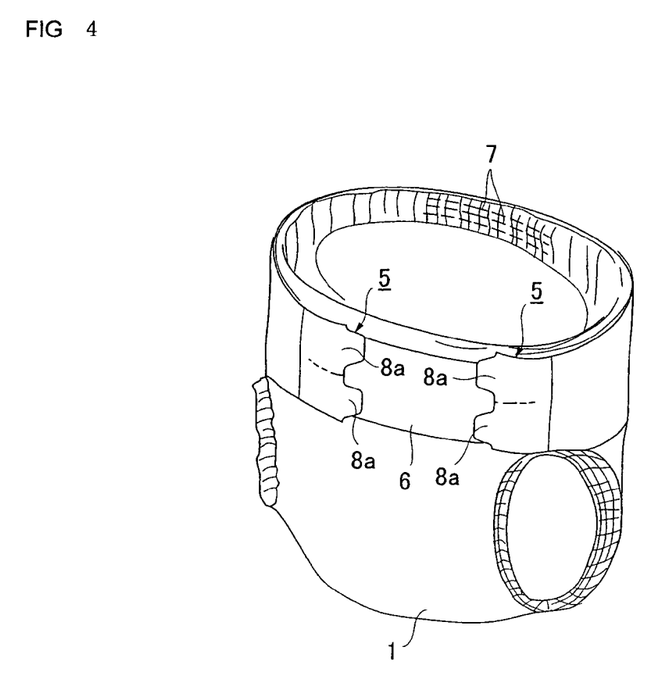
FIG. 4 shows a view showing the state, in which the paper diaper is worn by the ordinary fastening method.
Figure 5:
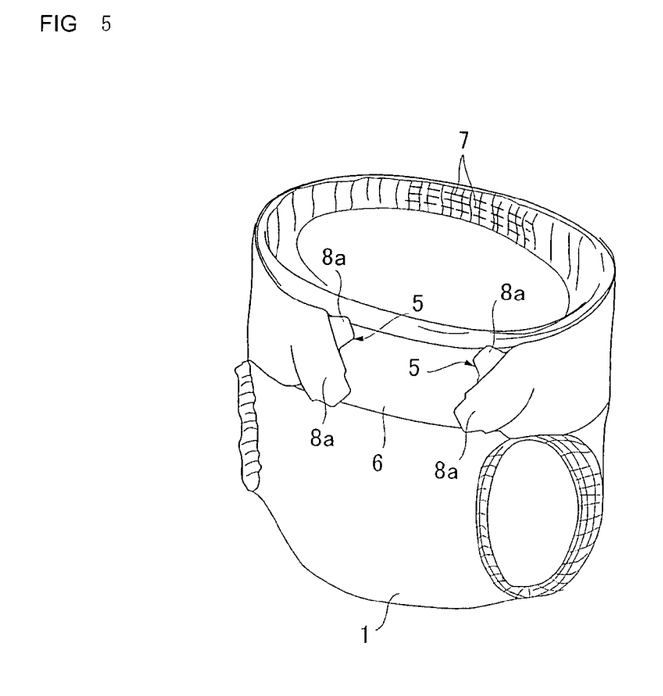
FIG. 5 shows a view showing the state, in which the paper diaper is worn by a cross fastening method.

In the invention, the fastening base sheet 8 is provided, at its portion between the joint ears 8*a* and 8*a*, with perforations 10, which extend in the horizontal direction from the outer side edge to the inner side. In case, therefore, the ordinary fastening method is selected for wearing the present disposable paper diaper, the perforations 10 are not torn, but the joint ears 8*a* and 8*a* are fastened on the front target tape 6, as shown in FIG. 4. In case the cross fastening method is selected, the perforations 10 are torn, and the upper and lower joint ears 8*a* and 8*a* are intersected and fastened, as shown in FIG. 5.

Figure 2:
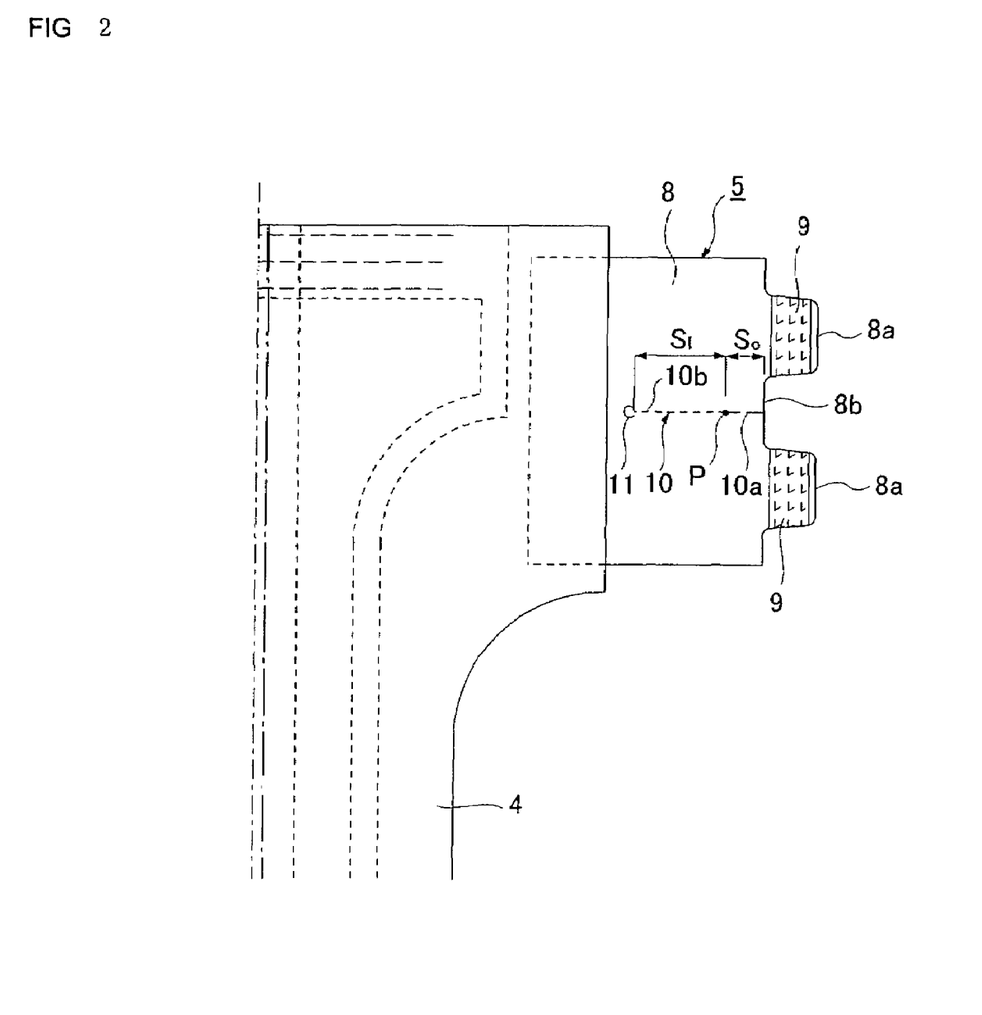
FIG. 2 shows an enlarged view of an essential portion of a fastening sheet 5 of the paper diaper.

In the perforations 10, as shown in FIG. 2, it is desired that a first perforation section 10*a* from the outer side edge to an intermediate point P is a high tearing strength section So having a relatively coarse perforation interval whereas a second perforation section 10*b* from the intermediate point P to the inner end is a low tearing strength section S.sub.I having a relatively fine perforation interval. As a result, the perforations are not accidentally torn, so long as the caretaker or wearer does not tear the perforations of the first perforation section 10*a*. In case the perforations 10 are torn to the intermediate point P by applying the force intentionally, the residual perforation 10*b* can be easily torn out.

In order to acquire the aforementioned effect, more specifically, the perforations intervals are adjusted such that the first perforation section 10*a* has a tearing strength of 3 to 10 N, preferably 4 to 8, whereas the second perforation section 10*b* has a tearing strength of 0.01 to 6 N, preferably 0.01 to 2 N.

In the inner end portion of the perforations 10, moreover, there is formed a C-shaped cut 11 for preventing the tear from that inner end. The cut 11 disperses, in case the perforations 10 are torn up to the inner end, the stress which is established at that inner end, thereby to prevent the fastening base sheet 8 from being torn out over the inner end of the perforations 10. Therefore, the shape should not be limited to that C-shape, so long the purpose to disperse the stress is achieved, but may be any shape such as a circular, elliptical or triangular shape.

Figure 3:
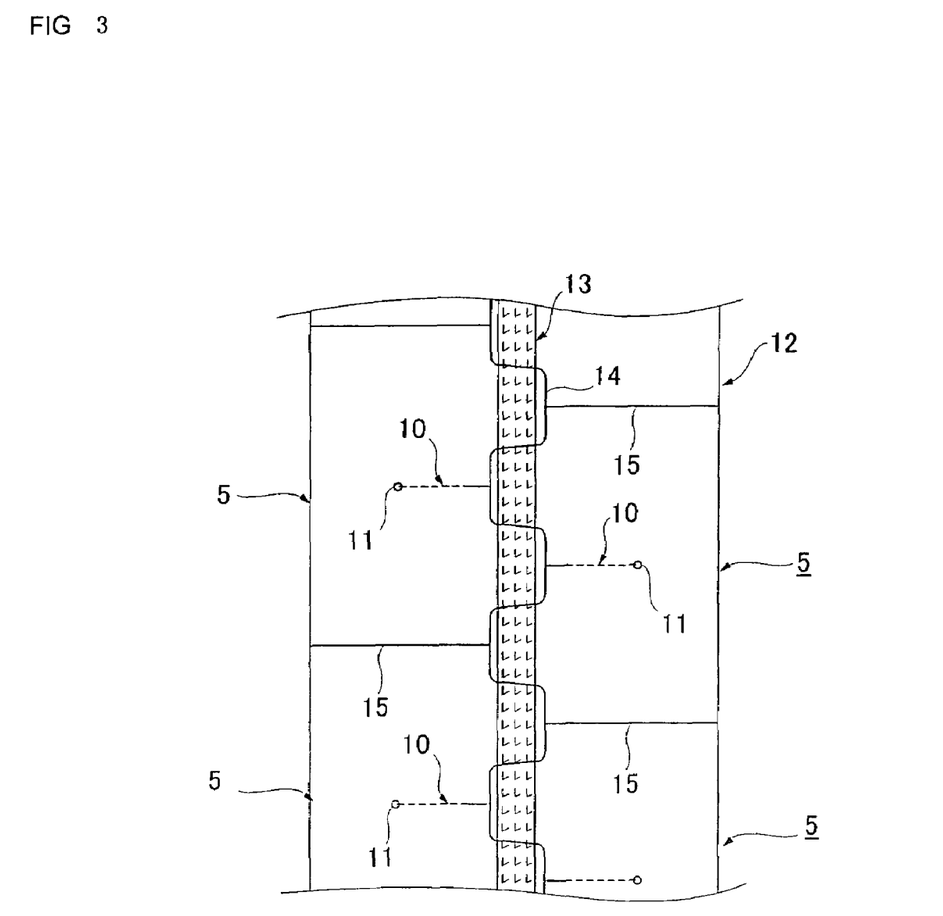
FIG. 3 shows a view showing a procedure for manufacturing the fastening sheet 5 by a zero-trim method.

In order to cope with the so-called "zero-trim" in the fastening sheet 5, on the other hand, notches 8*b* formed between the joint ears 8*a* and 8*a* of the two upper and lower stages may be formed to have a symmetric shape with respect to the shape of the joint ears 8*a*. As a result, the fastening sheet 5 can be manufactured in the so-called zero-trim, as shown in FIG. 3.

Specifically, a fastening base sheet 12 having a continuous web shape of a predetermined width is let off, and a facing fastener tape 13 is continuously adhered to the center position. Then, the fastening base sheet 12 is cut along an undulating periodic curve 14, which is so continuous in the direction of the fastening base sheet 12 as to cross the facing fastener 13 alternately. At the same time, cutting lines 15, 15, - - -, and so on for dividing the individual fastening sheets 5 and 5 are formed, and the perforations 10, 10, - - -, and so on are formed at predetermined positions at every fastening sheets 5, 5, - - -, and so on.

In the foregoing mode of embodiment, the joint ears 8*a* and the front target tape 6 are peelably jointed by the facing fasteners acting as mechanical fastener means. However, an adhesive layer may also be formed directly or indirectly through a sheet on the joint ears 8*a* so that they can be peelably adhered to the front target tape 6.

In the foregoing mode embodiment, the perforations 10 are formed along the horizontal direction from the outer side edge in the portion of the fastening sheet 8 between the joint ears 8*a* and 8*a*. However, the perforations 10 may also be either eccentrically formed on one of the upper and lower joint ears 8*a* and 8*a* or formed at an angle of inclination with respect to the outer side edge.

Figure 6:
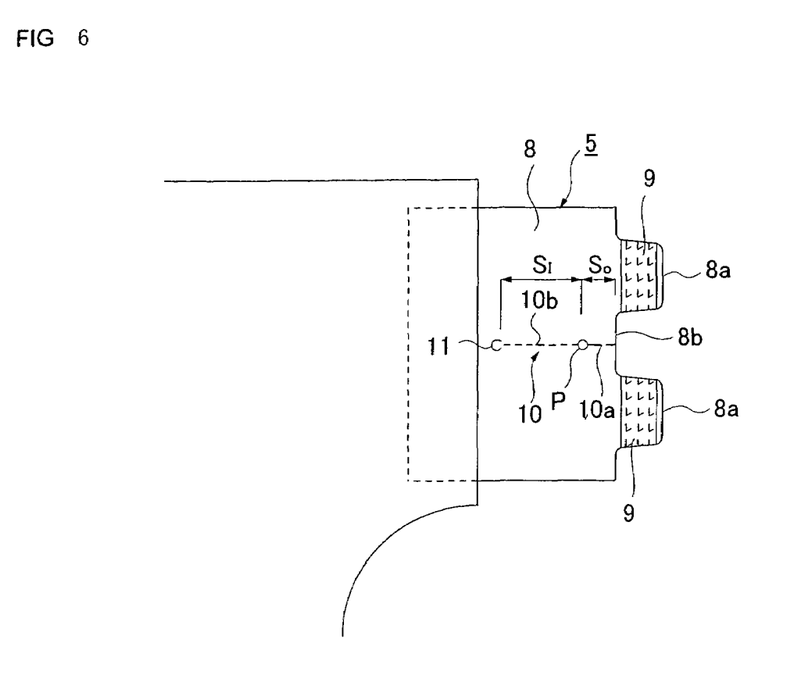
FIG. 6 shows an enlarged view of an essential portion of the fastening sheet 5 and showing another example of perforations 10.
Figure 7:
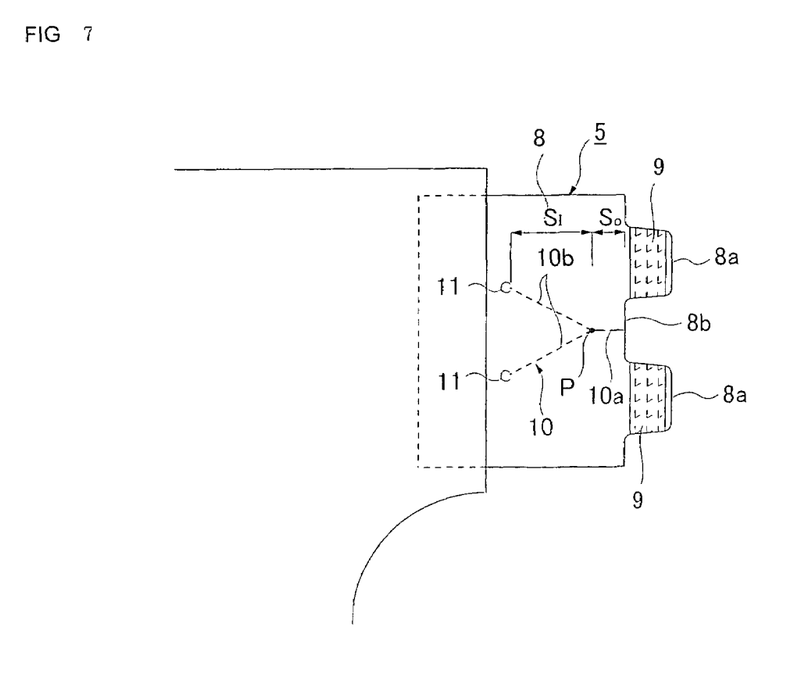
FIG. 7 shows an enlarged view of an essential portion of the fastening sheet 5 and showing another example of perforations 10.

In another example of forming the perforations 10, a round hole acting as a cushion at the tearing time may also be formed at the intermediate point P between the first perforation section 10*a* and the second perforation section 10*b*, as shown in FIG. 6. In order to enhance the degree of freedom for the upper and lower joint ears 8*a* and 8*a*, the second perforation section 10*b* from the intermediate point P to the inner end may also be branched in a lateral V-shape, as shown in FIG. 7. In this modification, the C-shaped cuts 11 and 11 are formed at the inner ends of the individual second perforations 10*b*.

The invention claimed is:

1. A disposable paper diaper comprising:
   a main diaper sheet having a back side portion with opposing side portions and an abdomen side portion;
   fastening sheets each respectively arranged at a respective one of said side portions of the back side of the paper diaper and each including:
   a fastening sheet outer side edge distal from said main diaper sheet;
   joint ears extending from the fastening sheet outer side edge to protrude sideward from the main diaper sheet from at an upper position and a lower position on said fastening sheet, said joint ears each having a joint ear inner side surface which faces toward an infant when the paper diaper is worn;
   one of adhesive layers or facing fasteners disposed on the joint ear inner side surfaces of said joint ears and removably fastenable to the abdomen side portion of the paper diaper so as to secure the diaper to the infant; and
   said fastening sheet defining perforations forming a tear line leading from the fastening sheet outer side edge at a position between said joint ears at said upper and lower positions and toward said main diaper sheet and to a perforations end point,
   wherein said perforations include:
   a first perforation section extending from the fastening sheet outer side edge to an intermediate point configured to form a first tear line section of said tear line as a high tearing strength section having a high tearing strength and a relatively coarse perforation interval and
   a second perforation section from said intermediate point toward said diaper main sheet and to said perforations end point, said second perforation section being configured to form a second tear line section as a low tearing strength section having a low tearing strength, less than said high tearing strength, and a relatively fine perforation interval which is finer than said coarse perforation interval.

2. The disposable diaper as set forth in claim 1, wherein said first perforation section has a tearing strength of 3 to 10 N, and wherein said second perforation section has a tearing strength of 0.01 to 6 N.

3. The disposable diaper as set forth in claim 2, wherein said perforations are configured at the perforations end point to resist tear out of said perforations end point.

4. The disposable diaper as set forth in claim 3, further comprising notches each respectively formed between said joint ears of the upper and lower positions and having a same shape as a shape of said joint ears.

5. The disposable diaper as set forth in claim 1, wherein said perforations are configured at the perforations end point to resist tear out of said perforations end point.

6. The disposable diaper as set forth in claim 5, further comprising notches each respectively formed between said joint ears of the upper and lower positions and having a same shape as a shape of said joint cars.

7. The disposable diaper as set forth in claim 1, further comprising notches each respectively formed between said joint ears of the upper and lower positions and having a same shape as a shape of said joint ears.

8. The disposable diaper as set forth in claim 1, wherein said joint ears are formed contiguously with said fastening sheets.

* * * * *